United States Patent [19]
Ray et al.

[11] Patent Number: 6,000,939
[45] Date of Patent: Dec. 14, 1999

[54] UNIVERSAL ALIGNMENT INDICATOR

[76] Inventors: Isaac Ray, 3700 Bedford Ave., Brooklyn, N.Y. 11229; Lawrence Avramenko, 3845 Lime Ave., Brooklyn, N.Y. 11224-1323

[21] Appl. No.: 09/246,588

[22] Filed: Feb. 8, 1999

[51] Int. Cl.⁶ .............................. A61C 1/00; A61C 3/00; A61C 3/02
[52] U.S. Cl. .................................. 433/27; 433/75; 433/76
[58] Field of Search .................................. 433/27, 75, 76, 433/72, 98, 215, 229

[56] References Cited

U.S. PATENT DOCUMENTS

| | | | |
|---|---|---|---|
| 3,218,624 | 11/1965 | Zane | 433/27 |
| 3,462,842 | 8/1969 | Greenberg et al. | 433/27 |
| 4,736,629 | 4/1988 | Cole | 73/517 R |
| 4,824,367 | 4/1989 | Rosentiel et al. | 433/27 X |
| 5,243,861 | 9/1993 | Kloeck et al. | 73/517 R |
| 5,383,364 | 1/1995 | Takahashi et al. | 73/517 R |
| 5,456,013 | 10/1995 | Elias | 433/27 X |
| 5,538,423 | 7/1996 | Coss et al. | 433/27 |
| 5,597,304 | 1/1997 | Ray et al. | 433/75 |
| 5,739,431 | 4/1998 | Petri | 73/509 |

*Primary Examiner*—Nicholas D. Lucchesi
*Attorney, Agent, or Firm*—Richard L. Miller, P.E

[57] ABSTRACT

An improved precise orientating tooth drilling device of a type having drill orientation apparatus attaching to a dental drill with a drill bit by a drill clamp and generating a drill angular position signal having a drill signal X-component and a drill signal Y-component and representing an angular position of the drill orientation apparatus, tooth orientation apparatus for removably attaching to a tooth and generating a tooth angular position signal having a tooth signal X-component and a tooth signal Y-component and representing an angular position of the tooth, comparing apparatus for, comparing the drill angular position signal and the tooth angular position signal to each other and determining if a difference therebetween is within a predetermined value, and an alarm alerting when the difference between the drill angular position signal and the tooth angular position signal is not within the predetermined value so that repositioning of the drill can be initiated. The improvement includes the drill angular position signal having a drill signal Z-component and the tooth angular position signal having a tooth signal Z-component.

11 Claims, 3 Drawing Sheets

UNIVERSAL ALIGNMENT INDICATOR

BACKGROUND OF THE INVENTION

1. Field of the Invention

The present invention relates to a universal alignment indicator. More particularly, the present invention relates to an improved universal alignment indicator.

2. Description of the Prior Art

Despite the sophistication of current dental technology, all dental operations are performed by hand and therefore their success depends totally on the experience and physical condition of the dentist.

Of extreme importance, is maintaining the dental drill in the desired angular position during the dental operation. This, however, can present a problem since both the dental drill and the patient are not stable in space and their orientation can be frequently changed during the dental operation. This will cause the drilling direction to change and present a serious deficit when specifically oriented holes must be drilled in a tooth.

During many dental operations it is often necessary to drill these specifically orientated holes in a tooth. For example, in order to provide an artificial crown for a tooth, the crown portion of the tooth is to first grind down to the root surface. Thereafter a peg or support, usually gold, for the artificial crown, is inserted into the root by means of specifically orientated holes drilled into the root.

Numerous innovations for dental drill orientating devices have been provided in the prior art that will be described. However, even though these innovations may be suitable for the specific individual purposes to which they address, they differ from the present invention in that they do not teach a dental drill alignment device that includes a first transducer attached to a dental drill for generating an angle signal, a second transducer affixed to a tooth for generating an angle signal, a central control unit for comparing the two angle signals to each other to be within a predetermined difference tolerance value, and an alarm for indicating when the two angle signals do not correspond within the predetermined difference tolerance value.

A FIRST EXAMPLE, U.S. Pat. No. 4,736,629 to Cole teaches the accelerometer comprises a substrate, a metallic movable plate, and a mounting system for mounting the movable plate such that it is positioned above the substrate and can rotate about a flexure axis that is above and is substantially parallel to the substrate. The flexure axis divides the sensing element into first and second sections. The total moments of the first and second sections about the flexure axis are different, such that acceleration normal to the substrate tends to rotate the sensing element about the flexure axis. A first electrode is mounted by the substrate adjacent the first section to form a first capacitor, and a second electrode is mounted by the substrate adjacent the second section to form a second capacitor. A detector for measuring the relative capacitances of the first and second capacitors is provided comprising an integrator, an inverting amplifier, and switches for periodically charging and discharging the capacitors in response to a clock signal. In one embodiment, the sensing element includes an internal opening, and the mounting system is positioned within the opening and includes a pedestal mounted to the substrate, and torsion bars and/or a beam connecting the pedestal to the sensing element. The sensing element preferably comprises a metallic plate, and the substrate preferably comprises a semiconductor upon which the detector and electrodes are fabricated in a single step process requiring no final assembly of components. In an embodiment adapted for high g applications, a pedestal divides a plate member into first and second cantilevered beams that flex in the same direction in response to a given acceleration.

A SECOND EXAMPLE, U.S. Pat. No. 5,243,861 to Kloeck et al. teaches a capacitive type semiconductor accelerometer has an intermediate silicon plate of n type conductivity including a movable electrode constituting a pendulum mass formed within the intermediate silicon plate and supported thereby via a beam so as to permit movement in a direction perpendicular to its plane. A first conductive island is formed within the intermediate plate and is immovably supported thereby via a first insulating leg so as to be isolated therefrom, and an upper glass plate is anodic bonded to the intermediate silicon plate. A first stationary electrode is formed on the upper glass plate at the position facing one face of the movable electrode with a predetermined gap. A lower glass plate is anodic bonded to the intermediate silicon plate and a second stationary electrode is formed on the lower glass plate at the position facing the other face of the movable electrode with a predetermined gap. First, second and third pads are disposed in common on the lower glass plate at the outside of the intermediate silicon plate, the first pad being electrically connected to the first stationary electrode via a first thin film lead formed on the lower glass plate and the first conductive island, the second pad being electrically connected to the movable electrode via a second thin film lead formed on the lower glass plate and the intermediate silicon plate and the third pad being electrically connected to the second stationary electrode via a third thin film lead formed on the lower glass plate.

A THIRD EXAMPLE, U.S. Pat. No. 5,383,364 to Takahashi et al. teaches an acceleration sensor comprises an upper semiconductor substrate having a rigid frame, four deformable beams connected with the rigid frame, and a weight portion supported by the plurality of deformable beams, a lower semiconductor substrate bonded to the rigid frame, a plurality of movable electrodes attached to the weight portion, and electrically isolated from one another, and a plurality of stationary electrodes attached to the second semiconductor substrate, and opposite to the plurality of movable electrodes for forming a plurality of variable capacitors, and the center of gravity of the weight portion is spaced from a common neutral surface of the four beams for allowing acceleration to produce bending moment exerted on the four beams, thereby causing the variable capacitors to independently change the capacitance.

A FOURTH EXAMPLE, U.S. Pat. No. 5,538,423 to Coss et al. teaches the present invention relates to a dental drilling system having a programmable control unit. The control unit controls operating parameters of the drilling system, such as the direction of rotation, the speed of rotation and the torque of a tool bit of a dental drill, as well as the irrigation fluid flow rate generated by a pump and the intensity of light generated by a light source. The control unit can be programmed with a number of sets of data values. Each set of data values represents a desired value for each of the operating parameters to be controlled. Also, each set of data values corresponds to a different step in a dental operation. Thus for each step of a dental operation, a surgeon can choose a desired set of operating parameter values from those sets that have been preprogrammed. The control unit then controls the operating parameters to achieve and maintain the values represented by the selected set of data values. Also, the control unit determines the electrical current and voltage applied to or generated by the drill motor to calculate the rotation speed and the torque at the tool bit. This enables the control unit to accurately achieve and maintain a specified rotation speed or torque. Applying a predetermined torque to a screw driving bit allows the dental drilling system to be used as a torque wrench.

A FIFTH EXAMPLE, U.S. Pat. No. 5,597,304, to Isaac Ray and Lawrence Avramenko of which the present invention is an improvement of, and which will be subsequently described in detail.

A SIXTH EXAMPLE, U.S. Pat. No. 5,739,431 to Petri teaches a magnetometer is integrated with a miniature vibrating beam accelerometer fabricated out of silicon on a common substrate. Dual pendulum-DETF force sensing accelerometers have integrated conductor coils on the pendulums that circulate alternating current to cause an additional pendulum motion also sensed by the DETF transducers for sensing local earth magnetic field. The integrated magnetic and acceleration sensing is used for each of three reference axes in a triaxial inclinometer magnetometer for borehole drill steering and surveying.

Our universal alignment indicator has a tooth portion 12 for attaching to a tooth a patient and a drill portion for attaching to a dental drill being held by a dentist.

The tooth portion includes a tooth clamp for removably mounting a gravity sensing tooth transducer to the tooth of the patient.

The gravity sensing tooth transducer senses its orientation, relative to vertical, and produces a tooth output signal that has a tooth signal "X"-component and a tooth signal "Y"-component.

The drill portion includes a drill clamp for mounting a gravity sensing drill transducer to the drill.

The gravity sensing drill transducer senses its orientation, relative to vertical, and produces a drill output signal that has a drill signal "X"-component and a drill signal "Y"-component.

In operation, the tooth portion is turned on and attached to the tooth. The gravity sensing tooth transducer senses the orientation of the tooth, relative to its "X"- coordinate and its "Y"-coordinate, and produces the tooth signal "X"-component and the tooth signal "Y"-component.

The tooth signal "X"-component and the tooth signal "Y"-component are digital or analog representations of the random tilt of the tooth, and which are fed to a central control unit where they are memorized.

Next, the drill portion is turned on. The gravity sensing drill transducer senses the orientation of the drill and produces the drill signal "X"-component and the drill signal "Y"-component which are digital or analog representations of the random tilt of the drill. These components are fed to the central control unit where they are memorized.

A desired tooth hole orientation line for a hole that is to be drilled in the tooth is arrived at by angular positioning the drill bit longitudinal axis of the drill bit collinear with the desired tooth hole orientation line for the hole.

The central control unit is then programmed with the "X" and "Y" coordinates of the desired difference angular orientation of the desired tooth hole orientation line, and a desired tolerance is set with tolerance value set control.

As the drilling proceeds, the central control unit constantly compares the tooth signal "X"-component, the tooth signal "Y"-component, the drill signal "X"-component, and the drill signal "Y"-component to determine that they are within acceptable value set of each other.

If, however, when either the tooth signal "X"-component, the tooth signal "Y"-component, the drill signal "X"-component, and the drill signal "Y"-component do not correspond respectively within desired predetermined difference value set with the tolerance value set control, indicating that the dentist and/or the patient have moved relative to each so that the drill bit longitudinal axis is no longer parallel with the desired tooth hole orientation line, an unbalance is present and an alarm signal is generated activating an alarm.

The alarm will continue until the tooth signal "X"-component, the tooth signal "Y"-component, the drill signal "X"-component, and the drill signal "Y"-component do correspond within the predetermined desired angular difference value input by tolerance value set control, indicating that the dentist and/or the patient have moved relative to each so that the drill bit longitudinal axis is now parallel with the desired tooth hole orientation line, and a balance is present.

The alarm can be audible and/or visual and may be a part of the central control unit utilizing the monitor for the visual alarm and a sound card for the audible alarm, but is not limited to that.

Depending upon the accuracy required during the operation on the tooth, a window of a predetermined amount can be provided in the central control unit. This window will prevent the alarm signal from being generated even when the tooth signal "X"-component, the tooth signal "Y"-component, the drill signal "X"-component, and the drill signal "Y"-component do not correspond within the predetermined desired angular difference tolerance value.

Furthermore, since any desired tooth hole orientation line for the hole can be readily maintained, multiple parallel holes can also be achieved without the need for additional apparatus, such as templates or the like, to be placed in the mouth of the patient.

It is apparent that numerous innovations for dental drill orientating devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide an improved universal alignment indicator that avoids the disadvantages of the prior art.

ANOTHER OBJECT of the present invention is to provide an improved universal alignment indicator that is simple and inexpensive to manufacture.

STILL ANOTHER OBJECT of the present invention is to provide an improved universal alignment indicator that is simple to use.

BRIEFLY STATED, YET ANOTHER OBJECT of the present invention is to provide an improved precise orientating tooth drilling device of a type having drill orientation means for attaching to a dental drill with a drill bit by a drill clamp and generating a drill angular position signal having a drill signal X-component and a drill signal Y-component and representing an angular position of the drill orientation means, tooth orientation means for removably attaching to a tooth and generating a tooth angular position signal having a tooth signal X-component and a tooth signal Y-component and representing an angular position of the tooth, comparing means comparing the drill angular position signal and the tooth angular position signal to each other and determining if a difference therebetween is within a predetermined value, and alarm means alerting when the difference between the drill angular position signal and the tooth angular position signal is not within the predetermined value so that repositioning of the drill can be initiated. The improvement includes the drill angular position signal having a drill signal Z-component and the tooth angular position signal having a tooth signal Z-component.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

Figures 1, 2:
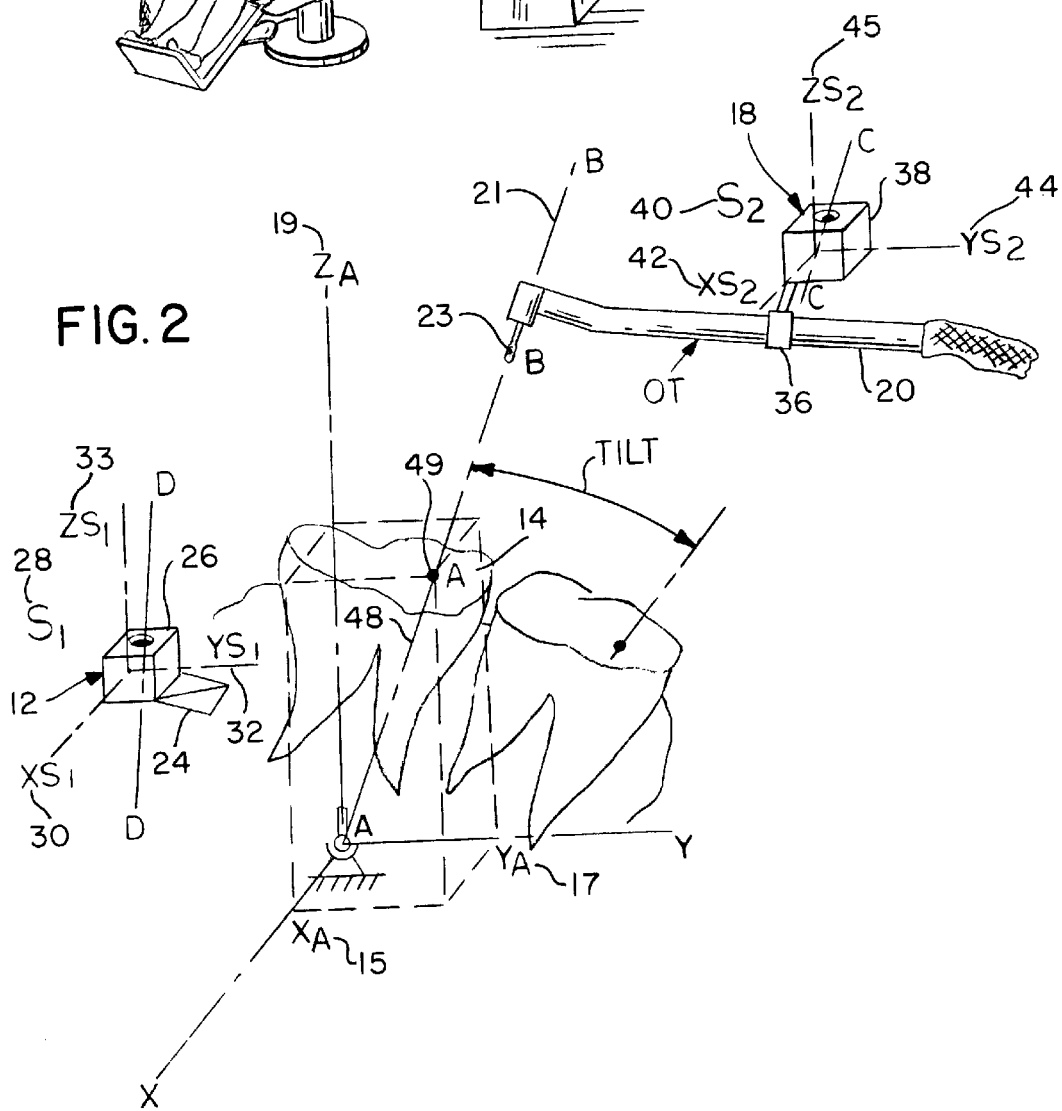
FIG. 1 is a diagrammatic perspective view illustrating a typical embodiment of the instant invention in use.
FIG. 2 is a diagrammatic view illustrating how some of the components of the instant invention cooperate with each other.

LIST OF REFERENCE NUMERALS UTILIZED IN THE DRAWING 10 improved universal alignment indicator of the present invention
12 tooth portion
14 tooth of patient 16
16 patient
18 drill portion
20 dental drill
21 drill bit longitudinal axis 21 of drill bit 23 of dental drill 20
22 dentist
23 drill bit of dental drill 20
24 tooth clamp of tooth portion 12 for removably mounting low frequency acceleration type sensor 26 to tooth 14 of patient 16
26 low frequency acceleration type sensor
28 tooth output signal of low frequency acceleration type sensor 26
30 tooth signal "X"-component of tooth output signal 28 of low frequency acceleration type sensor 26
32 tooth signal "Y"-component of tooth output signal 28 of low frequency acceleration type sensor 26
33 tooth signal "Z"-component of tooth output signal 28 of low frequency acceleration type sensor 26
36 drill clamp of drill portion 18 for mounting low frequency acceleration type sensor 38 to drill 20
38 low frequency acceleration type sensor
40 drill output signal of low frequency acceleration type sensor 38
42 drill signal "X"-component of drill output signal 40 of low frequency acceleration type sensor 38
44 drill signal "Y"-component of drill output signal 40 of low frequency acceleration type sensor 38
45 drill signal "Z"-component of drill output signal 40 of low frequency acceleration type sensor 38
46 programmable controller
47 foot switch for allowing operation when hands of dentist 22 are occupied
48 desired tooth hole orientation line for hole 49 drilled in tooth 14
49 hole drilled in tooth 14
50 tolerance value set control
51 mouse of tolerance value set control 50
52 drill power interrupt signal of drill power interrupter 54
54 drill power interrupter
55 solenoid valve of drill power interrupter 54
56 predetermined desired angular difference value input 56 of tolerance value set control 50
58 computer interface unit for interfacing programmable controller 46 with PC 60
60 PC
62 monitor of PC 60
64 bone structure 64 of patient 16
66 metallic tubing
68 template for attaching to bone structure 64 of patient 16
70 reference line

DETAILED DESCRIPTION OF THE PREFERRED EMBODIMENT

Referring now to the figures in which like numerals indicate like parts, and particularly to FIG. 1 the improved universal alignment indicator of the present invention is shown generally at 10 having a tooth portion 12 attached to a tooth 14 of a patient 16 and a drill portion 18 attached to a dental drill 20 being held by a dentist 22.

Figure 3:
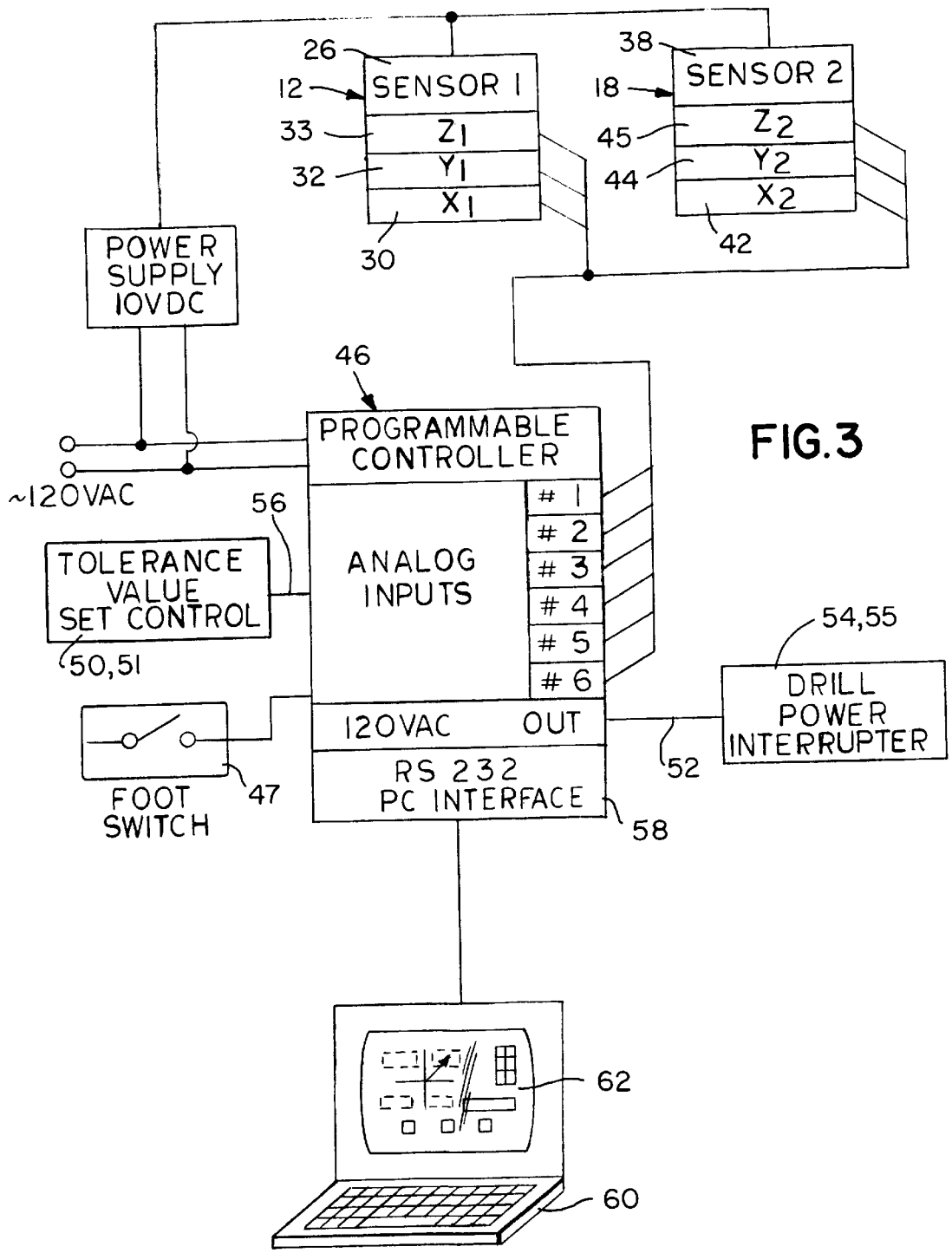
FIG. 3 is a block diagram thereof.

The configuration of the improved universal alignment indicator 10 can best be seen in FIGS. 2 and 3, and as such, will be discussed with reference thereto.

The tooth portion 12 includes a tooth clamp 24 for removably mounting a low frequency acceleration type sensor 26 to the tooth 14 of the patient 16.

The low frequency acceleration type sensor 26 is based upon capacitance change, since capacitance type sensors are free from interference of external magnetic fields and metal objects around.

The low frequency acceleration type sensor 26 senses its orientation and produces a tooth output signal 28 that has a tooth signal "X"-component 30, a tooth signal "Y"-component 32, and a tooth signal "Z"-component 33.

The drill portion 18 includes a drill clamp 36 for mounting a low frequency acceleration type sensor 38 to the drill 20.

The low frequency acceleration type sensor 38 is attached to the drill clamp 36 of the drill portion 18 by a quick disconnect for allowing sterilization of the drill 20, while the drill clamp 36 of the drill portion 18 is permanently attached to the drill 20.

The low frequency acceleration type sensor 38 is based upon capacitance change, since capacitance type sensors are free from interference of external magnetic fields and metal objects around.

The low frequency acceleration type sensor 38 senses its orientation and produces a drill output signal 40 that has a drill signal "X"-component 42, a drill signal "Y"-component 44, and a drill signal "Z"-component 45.

The improved universal alignment indicator 10 further comprises a foot switch 47 in electrical communication with a programmable controller 46 for allowing operation when the hands of the dentist 22 are occupied.

In operation, the tooth portion 12 is turned on and attached to the tooth 14. The low frequency acceleration type sensor 26 senses the orientation of the tooth 14, relative to its "X"-coordinate 15, its "Y"- coordinate 17, and its "Z"-coordinate 19, and produces the tooth signal "X"-component 30, the tooth signal "Y"-component 32, and the tooth signal "Z"-component 33.

The tooth signal "X"-component 30, the tooth signal "Y"-component 32, and the tooth signal "Z"-component 33 are analog representations of the random tilt of the tooth 14 which are fed to the programmable controller 46 where they are memorized.

Next the drill portion 18 is turned on. The low frequency acceleration type sensor 38 senses the orientation of the drill 20 and produces the drill signal "X"-component 42, the drill signal "Y"-component 44, and the drill signal "Z"-component, which are analog representations of the random tilt of the drill 20. These components are fed to the programmable controller 46 where they are memorized.

A desired tooth hole orientation line 48 for a hole 49 that is to be drilled in the tooth 14 is arrived at by angular positioning a drill bit longitudinal axis 21 of the drill bit 23 collinear with the desired tooth hole orientation line 48 for the hole 49. The programmable controller 46 is then programmed with the "X," "Y," and "Z" coordinates of the desired difference angular orientation of the desired tooth hole orientation line 48 and a desired tolerance is set with a tolerance value set control 50 which is preferably a mouse 51.

As the drilling proceeds, the programmable controller 46 constantly compares the tooth signal "X"-component 30, the tooth signal "Y"-component 32, the tooth signal "Z"-component 33, the drill signal "X"-component 42, the drill signal "Y"-component 44, and the drill signal "Z"-component 45 to determine that they are within acceptable value set of each other.

If, however, when either the tooth signal "X"-component 30, the tooth signal "Y"-component 32, the tooth signal "Z"-component 33, the drill signal "X"-component 42, the drill signal "Y"-component 44, and the drill signal "Z"-component 45 does not correspond, respectively, within desired predetermined difference value set with the tolerance value set control 50, indicating that the dentist 22 and/or the patient 16 have moved relative to each other so that the drill bit longitudinal axis 21 is no longer parallel with the desired tooth hole orientation line 48, an unbalance is present and a drill power interrupt signal 52 is generated by a drill power interrupter 54 which interrupts operation of the drill 20 by shutting off the compressed air to the drill 20, and which is preferably a solenoid valve 55.

The drill 20 will remain interrupted until the tooth signal "X"-component 30, the tooth signal "Y"-component 32, the tooth signal "Z"-component 33, the drill signal "X"-component 42, and the drill signal "Y"-component 44, and the drill signal "Z"-component 45 correspond within the predetermined desired angular difference value input 56 by tolerance value set control 50, indicating that the dentist 22 and/or the patient 16 have moved relative to each so that the drill bit longitudinal axis 21 is now parallel with the desired tooth hole orientation line 48, and a balance is present.

The improved universal alignment indicator 10 further comprises a computer interface unit 58 for interfacing the programmable controller 46 with a PC 60 having a monitor 62 which shows actual position of and image of the drill 20 in relation to the "X," "Y," and "Z" coordinates of the desired difference angular orientation of the desired tooth hole orientation line 48 and thereby shows an image of field of operation.

Depending upon the accuracy required during the operation on the tooth 14, a window of a predetermined amount can be provided in the programmable controller 46. This window will prevent the drill 20 from being interrupted even when the tooth signal "X"-component 30, the tooth signal "Y"-component 32, the tooth signal "Z"-component 33, the drill signal "X"-component 42, the drill signal "Y"-component 44, and the drill signal "Y"-component 45 do not correspond within the predetermined desired angular difference tolerance value.

Furthermore, since any desired tooth hole orientation line 48 for the hole 49 can be readily maintained, multiple parallel holes 49 can also be achieved without the need for additional apparatus, such as templates or the like, to be placed in the mouth of the patient 16.

Figure 4:
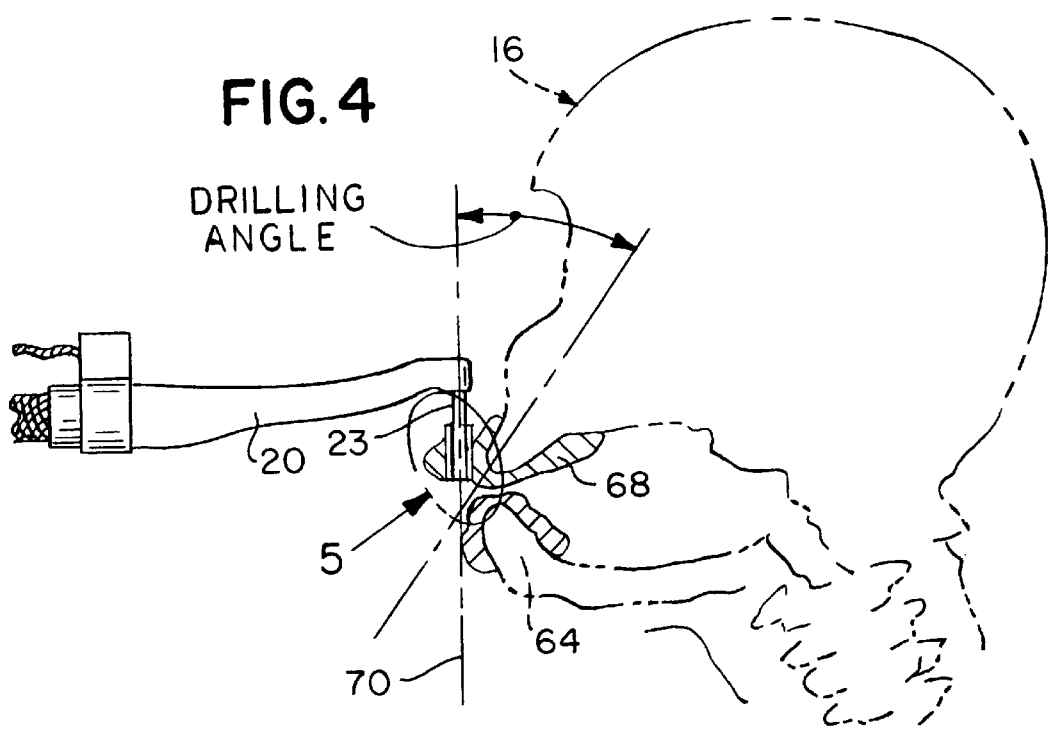
FIG. 4 is a diagrammatic view illustrating the drilling angle with reference to a patient's anatomy.
Figure 5:
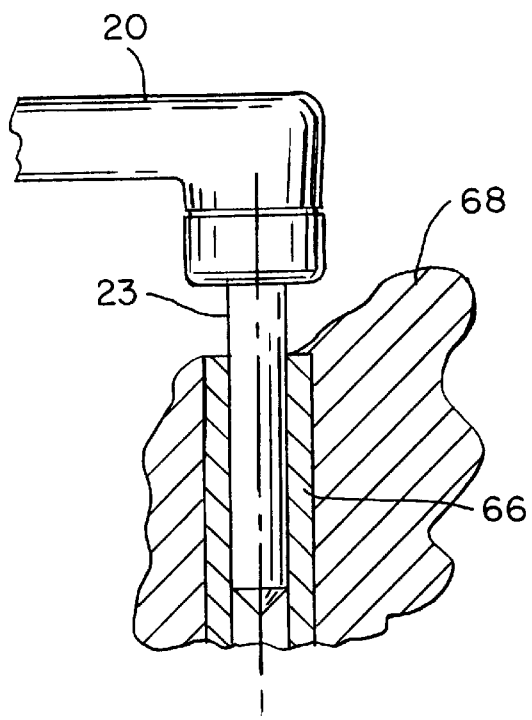
FIG. 5 is an enlarged diagrammatic cross sectional view of the area generally enclosed by the dotted curve identified by arrow 5 in FIG. 4 showing an acrylic template having a metallic tube therein.

Referring to FIGS. 4 and 5, in order to establish position of the drill bit 23 of the drill 20 in relation to bone structure 64 of the patient 16 during an implant operation, X-ray of the bone structure 64 of the patient 16 is performed with metallic tubing 66 attached to a template 68 for attaching to the bone structure 64 of the patient 16 and acting as a reference line 70 in 3D space.

The metallic tubing 66 has an inside diameter for accurately receiving the drill bit 23 of the drill 20.

The low frequency acceleration type sensor 26 and the low frequency acceleration type sensor 38 register position of the drill 20 in relation to the template 68 and the bone structure 64 of the patient 16 and subsequent X-ray images will allow establishing a proper drilling angle according to the dentist 22.

It will be understood that each of the elements described above, or two or more together, may also find a useful application in other types of constructions differing from the types described above.

While the invention has been illustrated and described as embodied in an improved universal alignment indicator, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An improved precise orientating tooth drilling device of a type having drill orientation means for attaching to a dental drill with a drill bit by a drill clamp and generating a drill angular position signal having a drill signal X-component and a drill signal Y-component and representing an angular position of the drill orientation means, tooth orientation means for removably attaching to a tooth and generating a tooth angular position signal having a tooth signal X-component and a tooth signal Y-component and representing an angular position of the tooth, comparing means comparing said drill angular position signal and said tooth angular position signal to each other and determining if a difference therebetween is within a predetermined value, and alarm means alerting when said difference between said drill angular position signal and said tooth angular position signal is not within said predetermined value so that repositioning of the drill can be initiated, said improvement comprising:

a) said drill angular position signal of said drill orientation means having a drill signal Z-component; and b) said tooth angular position signal of said tooth orientation means having a tooth signal Z-component.

2. The improvement as defined in claim 1, wherein said improvement further comprises said drill orientation means and said tooth orientation means being of a low frequency acceleration type based upon capacitance change, since capacitance type sensors are free from interference of external magnetic fields and metal objects around.

3. The improvement as defined in claim 1, wherein said improvement further comprises said drill orientation means being attachable to said drill clamp by a quick disconnect for allowing sterilization of the drill, while said drill clamp is permanently attached to the drill.

4. The improvement as defined in claim 1, wherein said improvement further comprises said comparing means being a programmable controller.

5. The improvement as defined in claim 1, wherein said improvement further comprises a computer interface unit for interfacing said comparing means with a PC having a monitor which shows actual position of and image of the drill in relation to "X," "Y," and "Z" coordinates of a desired difference angular orientation of a desired tooth hole orientation line and thereby shows an image of field of operation.

6. The improvement as defined in claim 1, wherein said improvement further comprises a drill power interrupter that generates a drill power interrupt signal which interrupts operation of the drill by shutting off the compressed air to the drill when said alarm means is activated.

7. The improvement as defined in claim 6, wherein said improvement further comprises said drill power interrupter being a solenoid valve.

8. The improvement as defined in claim 1, wherein said improvement further comprises a foot switch in electrical communication with said comparing means for allowing operation when the hands of the dentist are occupied.

9. The improvement as defined in claim 1, wherein said improvement further comprises a template for attaching to the bone structure of the patient, with said drill orientation means and said tooth orientation means registering position of the drill bit of the drill in relation to said template and the bone structure of the patient and subsequent X-ray images allow establishing a proper drilling angle according to the dentist.

10. The improvement as defined in claim 9, wherein said improvement further comprises a metallic tubing attached to said template and acting as a reference line in 3D space during X-raying to establish a position of the drill bit of the drill in relation to the bone structure of the patient during an implant operation.

11. The improvement as defined in claim 10, wherein said improvement further comprises said metallic tubing having an inside diameter for accurately receiving the drill bit of the drill.

* * * * *